(12) United States Patent
Parthasaradhi Reddy et al.

(10) Patent No.: US 7,947,840 B2
(45) Date of Patent: May 24, 2011

(54) PROCESS FOR PREPARATION OF ENANTIOMERICALLY PURE ESOMEPRAZOLE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 12/279,354

(22) PCT Filed: Sep. 25, 2007

(86) PCT No.: PCT/IN2007/000433
§ 371 (c)(1),
(2), (4) Date: Aug. 14, 2008

(87) PCT Pub. No.: WO2009/040825
PCT Pub. Date: Apr. 2, 2009

(65) Prior Publication Data
US 2010/0174087 A1    Jul. 8, 2010

(51) Int. Cl.
*C07D 401/12*    (2006.01)

(52) U.S. Cl. .................................................. 546/273.7

(58) Field of Classification Search ................ 546/273.7
See application file for complete search history.

(56) References Cited

FOREIGN PATENT DOCUMENTS

| WO | 9427988 A1 | 12/1994 |
|---|---|---|
| WO | 02098423 A1 | 12/2002 |
| WO | 2004002982 A2 | 1/2004 |
| WO | 2004099181 A1 | 11/2004 |
| WO | 2005105786 A1 | 11/2005 |
| WO | 2006120520 A1 | 11/2006 |
| WO | 2007013743 A1 | 2/2007 |

*Primary Examiner* — Patricia Morris
(74) *Attorney, Agent, or Firm* — Caesar, Rivise, Bernstein, Cohen & Pokotilow, Ltd.

(57) ABSTRACT

The present invention provides an improved and commercially viable process for preparation of substantially enantiomerically pure esomeprazole in neutral form or as a pharmaceutically acceptable salt or as its solvates including hydrates. Thus, for example, a compound containing a mixture of 1-(S)-camphorsulfonyl-5-methoxy-2-[(3,5-dimethyl-4-methoxy-2-pyridyl)methyl-(S)-sulfinyl]-1H-benzimidazole and 1-(S)-camphorsulfonyl-6-methoxy-2-[(3,5-dimethyl-4-methoxy-2-pyridyl)methyl-(S)-sulfinyl]-1H-benzimidazole is hydrolyzed with barium hydroxide, isolated the resulting esomeprazole barium salt followed by neutralization with an acid to yield substantially enantiomerically pure esomeprazole in neutral form and then converted into its pharmaceutically acceptable salts.

27 Claims, No Drawings

PROCESS FOR PREPARATION OF ENANTIOMERICALLY PURE ESOMEPRAZOLE

FIELD OF THE INVENTION

The present invention provides an improved and commercially viable process for preparation of substantially enantiomerically pure esomeprazole in neutral form or as a pharmaceutically acceptable salt or as its solvates including hydrates.

BACKGROUND OF THE INVENTION

Omeprazole, chemically 5-methoxy-2-[[(4-methoxy-3,5-dimethyl-2-pyridinyl)methyl]sulfinyl]-1H-benzimidazole and its therapeutic uses are disclosed in European Patent No. 5129. Omeprazole is a well-known gastric acid secretion inhibitor, and is useful as an anti ulcer agent. Omeprazole has a stereogenic center at sulfur and therefore exist as two optical isomers such as R-omeprazole and S-omeprazole (esomeprazole).

The resolution processes of racemates of Substituted 2-(2-pyridinylmethylsulfinyl)-1H-benzimidazoles were for example disclosed in DE 4035455 and PCT Publication No. WO 94/27988. According to these processes chiral ether such as fenchyloxymethyl or chiral acyloxy methyl group such as mandeloyl- is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We find that these intermediates are difficult to prepare and involve in many steps.

PCT Publication No. WO 02/098423 relates to an inclusion complex of (S)-omeprazole with cyclodextrins. The process comprises adding a cyclodextrin to an aqueous solution of a substantially pure optical isomer of a benzimidazole compound or a pharmaceutically acceptable salt thereof, and isolating the inclusion complex so formed from the solution.

The resolution of sulfoxide compounds including racemic omeprazole were described in PCT Publication No. WO 2004/002982. The method requires expensive reagents like titanium compounds, two chiral reagents namely diethyl-D-tartarate and L-Mandelic acid.

Enantioselective synthesis is described for example in Euro. J. Biochem. 166 (1987) 453 and U.S. Pat. No. 5,948,789. Disadvantages of these methods are that strict control of conditions is to be maintained and strict control of quantities of oxidizing agents is required for avoiding oxidation of desired sulfoxide to sulfone impurity. Moreover, these methods require expensive reagents like titanium isoproxide and diethyl-D-tartarate.

The alkaline salts of (S)-enantiomer of omeprazole (esomeprazole), the pharmaceutical preparations of these salts and the method of treatment of gastric acid-related diseases using them are disclosed in U.S. Pat. Nos. 4,738,974, 5,877,192 and 5,714,504.

PCT Publication No. WO 2004/099181 A1 described a barium salt of the (S)-enantiomer of omeprazole, process for preparing the said barium salt, pharmaceutical compositions comprising the salt and a method of treatment of gastrointestinal ulcers comprising administration of the salt.

PCT Publication No. WO 2004/099182 A1 described a zinc salt of the (S)-enantiomer of omeprazole, process for preparing the said zinc salt, pharmaceutical compositions comprising the salt and a method of treatment of gastrointestinal ulcers comprising administration of the salt.

PCT Publication No. WO 2006/120520 A1 described a strontium salt of esomeprazole and a process for preparing it, which comprises reacting esomeprazole free base or a sodium, potassium or lithium salt of esomeprazole with a strontium source.

PCT Publication No. WO 2005/105786 A1 disclosed a stereoselective process for preparing substituted sulfoxides, which comprises reacting racemic omeprazole with (S)-camphorsulfonyl chloride to form a diastereomeric mixture, separating the diastereomers by fractional crystallization followed by deprotection to give esomeprazole.

PCT Publication No. WO 2005/116011 A1 disclosed a process for stereoselective synthesis of substituted sulfoxides, wherein 5-methoxy-2-[[(4-methoxy-3,5-dimethyl-2-pyridinyl)methyl]thio]-1H-benzimidazole is reacted with (R)-camphorsulfonyl chloride to form a mixture of 1-(R)-camphorsulfonyl-5- (and 6-)methoxy-2-[(3,5-dimethyl-4-methoxy-2-pyridyl)methylthio]-1H-benzimidazole, oxidized to obtain a diastereomeric excess of 1-(R)-camphorsulfonyl-(5- and 6-)-methoxy-2-[(3,5-dimethyl-4-methoxy-2-pyridyl)methyl-(S)-sulfinyl]-1H-benzimidazole over 1-(R)-camphorsulfonyl-(5- and 6-)-methoxy-2-[(3,5-dimethyl-4-methoxy-2-pyridyl) methyl-(R)-sulfinyl]-1H-benzimidazole, the diastereomers are separated by fractional crystallization and the separated 1-(R)-camphorsulfonyl-(5- and 6-)-methoxy-2-[(3,5-dimethyl-4-methoxy-2-pyridyl) methyl-(S)-sulfinyl]-1H-benzimidazole is deprotected to give esomeprazole.

PCT Publication No. WO 2007/013743 A1 disclosed a process for preparing optically pure esomeprazole which comprises dissolving (S)-(−)-binol, a weak base and the racemic form of omeprazole in a mixture of a water-compatible organic solvent and water at a high temperature, cooling the mixed solution to crystallize the inclusion complex of esomeprazole and (S)-(−)-binol, and removing the (S)-(−)-binol moiety from the crystallized inclusion complex.

However, a need still remains for an improved and commercially viable process for preparing enantiomerically pure esomeprazole that should solve the aforesaid problems associated with processes described in the prior art, which will be suitable for large-scale preparation, in terms of simplicity, chemical yield and purity of the product.

The object of the present invention is to provide an improved and commercially viable process for preparation of substantially enantiomerically pure esomeprazole in neutral form or as a pharmaceutically acceptable salt or as its solvates including hydrates.

DETAILED DESCRIPTION OF THE INVENTION

In accordance with the present invention, there is provided a process for preparation of substantially enantiomerically pure esomeprazole of formula I:

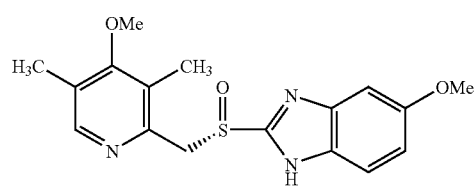

or a pharmaceutically acceptable salt thereof; which comprises:
a) hydrolyzing a diastereomeric compound containing a mixture of 1-(S)-camphorsulfonyl-5-methoxy-2-[(3,5-dimethyl-4-methoxy-2-pyridyl)methyl-(S)-sulfinyl]-1H-benzimidazole and 1-(S)-camphorsulfonyl-6-methoxy-2-[(3, 5-dimethyl-4-methoxy-2-pyridyl)methyl-(S)-sulfinyl]-1H-benzimidazole of formula II:

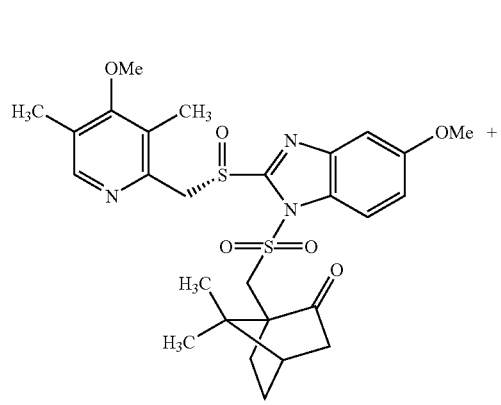

contaminated with an undesired diastereomeric compound containing a mixture of 1-(S)-camphorsulfonyl-5-methoxy-2-[(3,5-dimethyl-4-methoxy-2-pyridyl)methyl-(R)-sulfinyl]-1H-benzimidazole and 1-(S)-camphorsulfonyl-6-methoxy-2-[(3,5-dimethyl-4-methoxy-2-pyridyl)methyl-(R)-sulfinyl]-1H-benzimidazole of formula III:

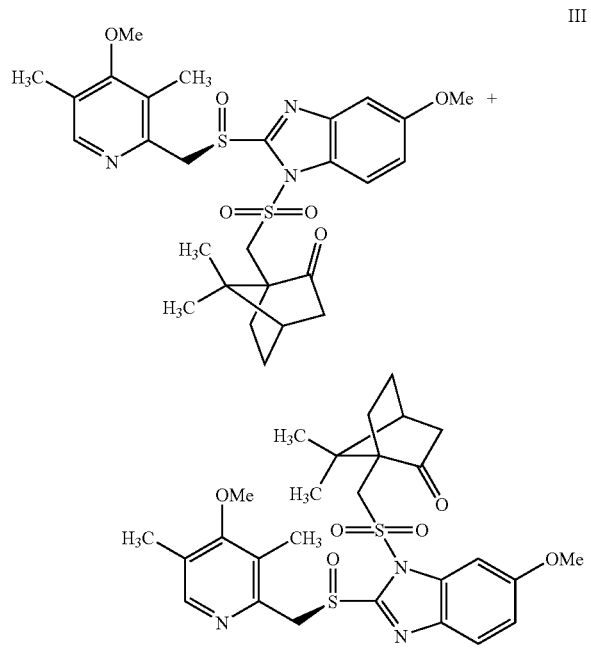

with an hydroxide base selected from the group consisting of barium hydroxide, strontium hydroxide and cesium hydroxide, in a suitable solvent to give the corresponding esomeprazole salts of formulae $IV_a$, $IV_b$ or $IV_c$:

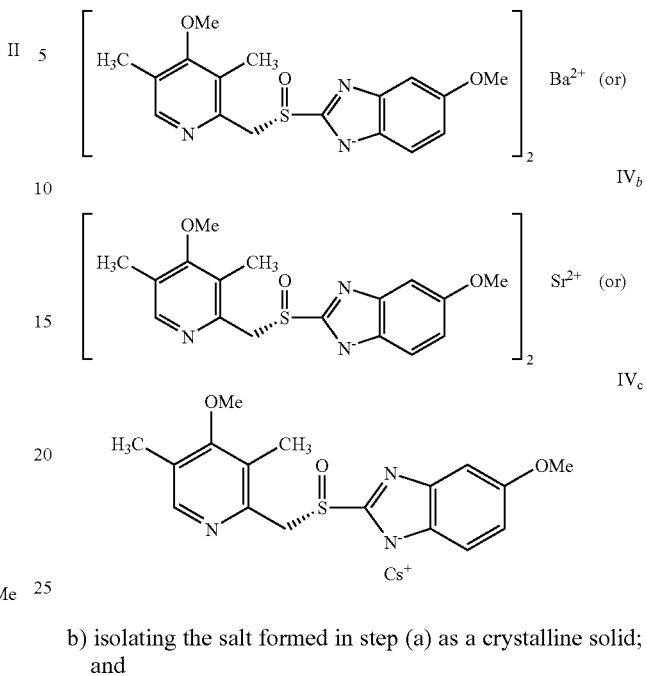

b) isolating the salt formed in step (a) as a crystalline solid; and c) neutralizing the esomeprazole salt formed in step (b) with an acid to obtain substantially enantiomerically pure esomeprazole of formula I and optionally converting esomeprazole formed into pharmaceutically acceptable salts of esomeprazole.

The term "substantially enantiomerically pure esomeprazole" refers to the esomeprazole having the content of isomeric impurity (R-omeprazole) in less than about 0.1% by weight measured by High Performance Liquid Chromatography (HPLC), preferably less than about 0.05% by weight and still more preferably having no traces of the isomeric impurity.

The term "diastereomeric compound of formula II contaminated with undesired diastereomeric compound of formula III" refers to the compound of formula II containing the content of undesired diastereomeric compound of formula III in about above 0.1% or above and up to 45% by weight. Preferable hydroxide base used in step (a) is barium hydroxide or strontium hydroxide.

The diastereomeric compound of formula II is used as starting material may be obtained by processes described in the art, for example by the processes described in the PCT Publication Nos. WO 2005/105786 A1 and WO 2005/116011 A1.

The suitable solvent used in the reaction in step (a) is selected from the group consisting of an ester solvent such as ethyl acetate, methyl acetate, isopropyl acetate, tert-butyl methyl acetate and ethyl formate; an alcoholic solvent such as methanol, ethanol and isopropyl alcohol; acetonitrile; tetrahydrofuran; dimethylformamide; dimethylsulfoxide; dioxane; an aromatic hydrocarbon solvent such as benzene, toluene, xylene; a halogenated hydrocarbon solvent such as methylene chloride, chloroform, carbontetrachloride, ethylene dichloride; a ketonic solvent such as acetone, methyl ethyl ketone, methyl isobutyl ketone, diethyl ketone; an ether solvent such as tert-butyl methyl ether, diethyl ether; diethyl carbonate; and a mixture thereof. Preferable solvent is an alcoholic solvent or a ketonic solvent, and more preferable solvent is methanol, ethanol or isopropyl alcohol.

The reaction in step (a) may be carried out at below 30° C., preferably carried out between 0° C. and 20° C. and more preferably carried out between 0° C. and 15° C.

Isolation of esomeprazole salt in step (b) may be carried out by methods usually known in the art such as cooling, partial removal of the solvent from the solution, addition of precipitating solvent or a combination thereof.

The acid used in step (c) may be an organic or inorganic acid. Preferable organic acid is selected from the group consisting of carboxylic acids such as acetic acid and formic acid; and sulfonic acids such as methane sulfonic acid. Most preferable organic acid is acetic acid. Preferable inorganic acid is a mineral acid such as sulfuric acid, hydrochloric acid and phosphoric acid.

Preferably aqueous solution of acid may be used for neutralization and more preferably dilute aqueous acid may be used.

The neutralization reaction in step (c) may preferably be carried out in a solvent system containing water and an organic solvent. Suitable organic solvent is selected from the group consisting of ester solvents such as ethyl acetate, methyl acetate, isopropyl acetate, tert-butyl methyl acetate and ethyl formate; halogenated hydrocarbon solvents such as methylene chloride, chloroform, carbontetrachloride, ethylene dichloride; and hydrocarbon solvents such as benzene, toluene, xylene. More preferable organic solvent is methylene chloride, chloroform or ethyl acetate.

The neutralization reaction in step (c) may preferably be carried out at below 40° C., more preferably carried out between 0° C. and 30° C. and still more preferably carried out between 0° C. and 20° C.

The enantiomerically pure esomeprazole of formula I obtained in step (c) can be converted into pharmaceutically acceptable salts by conventional methods.

Preferable pharmaceutically acceptable salts of esomeprazole are those of lithium, sodium, potassium, magnesium and calcium, and their solvates including hydrates thereof.

The following examples are given for the purpose of illustrating the present invention and should not be considered as limitations on the scope or spirit of the invention.

REFERENCE EXAMPLES

Reference Example 1

Racemate of 5-Methoxy-2-[(3,5-dimethyl-4-methoxy-2-pyridyl)methylsulfinyl]-1-H-benzimidazole (15 gm) was dissolved in dichloromethane (150 ml) and N,N-diisopropylethylamine (8.5 gm) was added to the solution. The solution was cooled to 0-5° C. (S)-Camphor sulfonyl chloride (13.3 gm) dissolved in 25 ml of methylenechloride was added slowly for one hour at 0° C.-5° C. The reaction mixture was maintained at 0° C.-5° C. for 3 hours. The pH was adjusted to 6.0-6.5 with acetic acid, then ice-cooled water (60 ml) was added. The layers were separated. The organic layer was washed with 10% aqueous sodium chloride. The organic layer was distilled under reduced pressure to obtain a residue containing the diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (23 gm).

Reference Example 2

The residue (23 gm) obtained in reference example 1 was stirred with isopropyl alcohol (60 ml) for 2 hours at 25° C. and then refluxed for 1 hour. The solution was cooled to 25° C. and maintained for 3 hours. The solid obtained was collected by filtration. The solid was stirred in methanol (90 ml) for 30 min and filtered to obtain 8.1 gm of a mixture of 1-(S)-camphor sulfonyl-5-methoxy-2-[(3,5-dimethyl-4-methoxy-2-pyridyl)methyl-(S)-sulfinyl]-1H-benzimidazole and 1-(S)-camphorsulfonyl-6-methoxy-2-[(3,5-dimethyl-4-methoxy-2-pyridyl)methyl-(S)-sulfinyl]-1H-benzimidazole (Content of the mixture of 1-(S)-camphorsulfonyl-5-methoxy-2-[(3,5-dimethyl-4-methoxy-2-pyridyl)methyl-(R)-sulfinyl]-1H-benzimidazole and 1-(S)-camphorsulfonyl-6-methoxy-2-[(3,5-dimethyl-4-methoxy-2-pyridyl)methyl-(R)-sulfinyl]-1H-benzimidazole: 12%).

EXAMPLES

Example 1

Step-I:
Methanol (300 ml) is added to a compound containing a mixture of 1-(S)-camphorsulfonyl-5-methoxy-2-[(3,5-dimethyl-4-methoxy-2-pyridyl)methyl-(S)-sulfinyl]-1H-benzimidazole and 1-(S)-camphorsulfonyl-6-methoxy-2-[(3,5-dimethyl-4-methoxy-2-pyridyl)methyl-(S)-sulfinyl]-1H-benzimidazole (30 gm, obtained as per the process described in reference example 2) under stirring at 25-30° C., the contents are cooled to 0-5° C., and then the solution of $Ba(OH)_2 \cdot 8H_2O$ (60 gm) in methanol (300 ml) is added slowly for 30 minutes at 0-5° C. The resulting mass is stirred for 30 minutes at 0-5° C., filtered the solid, washed with chilled methanol (15 ml) and then dried at 50-60° C. to give 15.2 gm of pure esomeprazole barium salt (enantiomeric purity: 100%).

Step-II:
Methylene chloride (225 ml) and water (90 ml) are added to esomeprazole barium salt (15.2 gm, obtained in step-I) under stirring at 25-30° C., the contents are cooled to 15° C. and then pH of the mass is adjusted to 6.5-7.0 with acetic acid. The resulting mass is stirred for 15 minutes, separated the layers and the aqueous layer is extracted with methylene chloride (100 ml). The total organic layer is washed with 5% NaCl solution (100 ml), dried over sodium sulfate and the resulting organic layer is distilled under vacuum at 40° C. and then co-distilled with methanol (100 ml) to give 13.1 gm of pure esomeprazole as residue (enantiomeric purity: 100%).

Step-III:
Methanol (26 ml) is added to the residue (13.1 gm, obtained in step-II) under stirring at 25-30° C., the contents are cooled to 10-15° C. and then the solution of sodium hydroxide (3.25 gm) in methanol is added for 15-30 minutes at 10° C. The resulting mass is stirred for 20 minutes, the temperature of the mass is raised to 25-30° C. and then stirred for 10 hours at 25-30° C. The reaction mass is cooled to 5-10° C. and then stirred for 1 hour. Filtered the solid, washed with chilled methanol (13 ml) followed by diisopropyl ether (50 ml) and then dried at 50-55° C. to give 10.2 gm of esomeprazole sodium salt (enantiomeric purity: 100%).

Example 2

Step-I:
Methanol (300 ml) is added to a compound containing a mixture of 1-(S)-camphorsulfonyl-5-methoxy-2-[(3,5-dimethyl-4-methoxy-2-pyridyl)methyl-(S)-sulfinyl]-1H-benzimidazole and 1-(S)-camphorsulfonyl-6-methoxy-2-[(3,5-dimethyl-4-methoxy-2-pyridyl)methyl-(S)-sulfinyl]-1H-benzimidazole (30 gm, obtained as per the process described in reference example 2) under stirring at 25-30° C., the contents are cooled to 0-5° C., and then the solution of $Sr(OH)_2 \cdot 8H_2O$ (51.4 gm) in methanol (300 ml) is added slowly for 30 minutes at 0-5° C. The resulting mass is stirred for 30 minutes at 0-5° C., filtered the solid, washed with chilled methanol (15 ml) and then dried at 50-60° C. to give 15.9 gm of pure esomeprazole strontium salt (enantiomeric purity: 100%).

Step-II:

Methylene chloride (235 ml) and water (95 ml) are added to esomeprazole strontium salt (15.9 gm, obtained in step-I) under stirring at 25-30° C., the contents are cooled to 15° C. and then pH of the mass is adjusted to 6.5-7.0 with acetic acid. The resulting mass is stirred for 15 minutes, separated the layers and the aqueous layer is extracted with methylene chloride (100 ml). The total organic layer is washed with 5% NaCl solution (100 ml), dried over sodium sulfate and the resulting organic layer is distilled under vacuum at 40° C. and then co-distilled with methanol (100 ml) to give 13.5 gm of pure esomeprazole as residue (enantiomeric purity: 100%).

Step-III:

Methanol (26 ml) is added to the residue (13.5 gm, obtained in step-II) under stirring at 25-30° C., the contents are cooled to 10-15° C. and then the solution of sodium hydroxide (3.25 gm) in methanol is added for 15-30 minutes at 10° C. The resulting mass is stirred for 20 minutes, the temperature of the mass is raised to 25-30° C. and then stirred for 10 hours at 25-30° C. The reaction mass is cooled to 5-10° C. and then stirred for 1 hour. Filtered the solid, washed with chilled methanol (13 ml) followed by diisopropyl ether (50 ml) and then dried at 50-55° C. to give 10.4 gm of esomeprazole sodium salt (enantiomeric purity: 100%).

We claim:

1. A process for preparation of substantially enantiomerically pure esomeprazole of formula I:

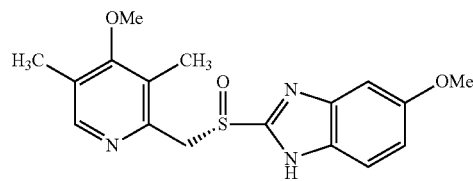

I or a pharmaceutically acceptable salt thereof; which comprises:

a) hydrolyzing a diastereomeric compound containing a mixture of 1-(S)-camphorsulfonyl-5-methoxy-2-[(3,5-dimethyl-4-methoxy-2-pyridy)methyl-(S)-sulfinyl]-1H-benzimidazole and 1-(S)-camphorsulfonyl-6-methoxy-2-[(3,5-dimethyl-4-methoxy-2-pyridyl)methyl-(S)-sulfinyl]-1H-benzimidazole of formula II:

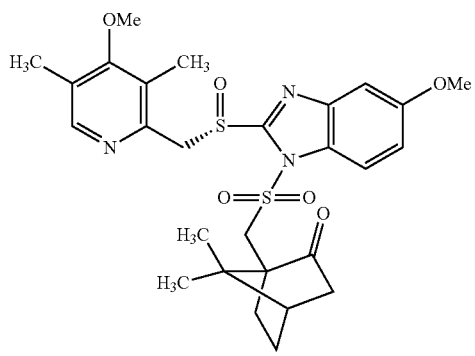

II

+

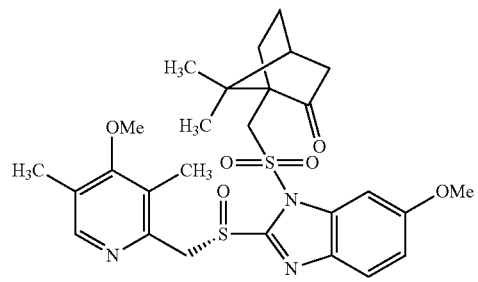

contaminated with an undesired diastereomeric compound containing a mixture of 1-(S)-camphorsulfonyl-5-methoxy-2-[(3,5-dimethyl-4-methoxy-2-pyridyl)methyl-(R)-sulfinyl]-1H-benzimidazole and 1-(S)-camphor sulfonyl-6-methoxy-2-[(3,5-dimethyl-4-methoxy-2-pyridyl)methyl-(R)-sulfinyl]-1H-benzimidazole of formula III:

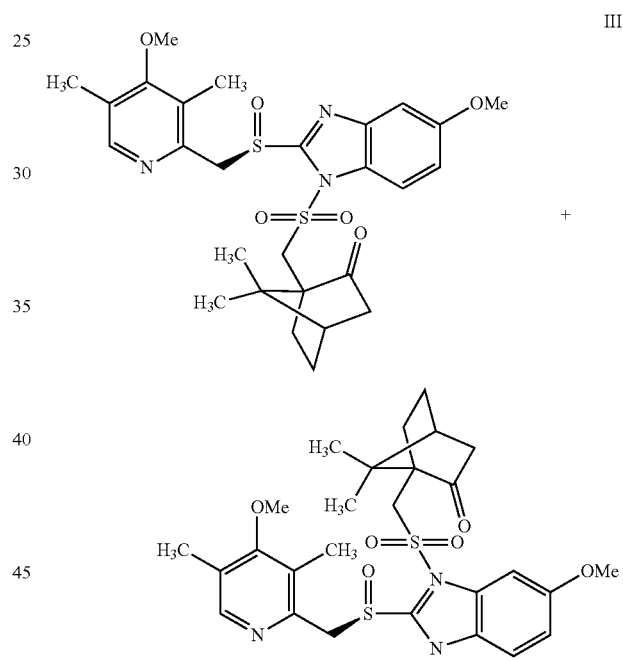

III with an hydroxide base selected from the group consisting of barium hydroxide, strontium hydroxide and cesium hydroxide, in a solvent to give the corresponding esomeprazole salts of formulae IV$_a$, IV$_b$ or IV$_c$:

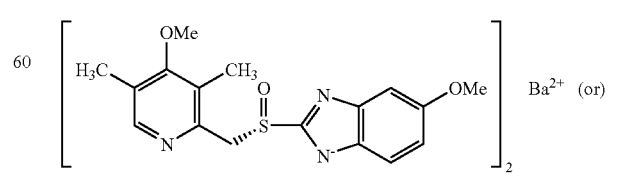

IV$_a$

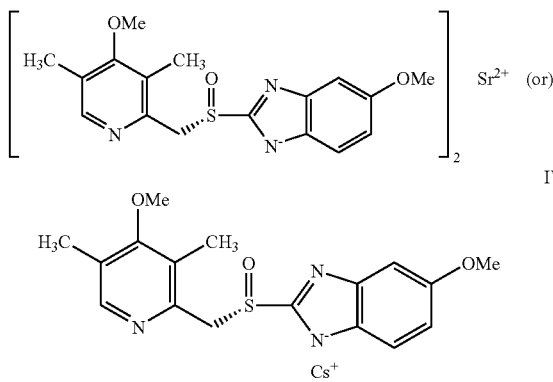

b) isolating the salt formed in step (a) as a crystalline solid; and c) neutralizing the esomeprazole salt formed in step (b) with an acid to obtain substantially enantiomerically pure esomeprazole of the formula I.

2. The process as claimed in claim 1, wherein the hydroxide base is barium hydroxide or strontium hydroxide.

3. The process as claimed in claim 1, wherein the solvent used in step (a) is an ester solvent, an alcoholic solvent, acetonitrile, tetrahydrofuran, dimethylformamide, dimethylsulfoxide, dioxane an aromatic hydrocarbon solvent, a halogenated hydrocarbon solvent, a ketonic solvent, an ether solvent, and mixtures thereof.

4. The process as claimed in claim 3, wherein the solvent is an alcoholic solvent or a ketonic solvent.

5. The process as claimed in claim 4, wherein the solvent is methanol, ethanol or isopropyl alcohol.

6. The process as claimed in claim 1, wherein the reaction in step (a) is carried out at below 30° C.

7. The process as claimed in claim 6, wherein the reaction is carried out between 0° C. and 20° C.

8. The process as claimed in claim 7, wherein the reaction is carried out between 0° C. and 15° C.

9. The process as claimed in claim 1, wherein the acid used in step (c) is an organic or inorganic acid.

10. The process as claimed in claim 9, wherein the organic acid is selected from the group consisting of carboxylic acids and sulfonic acids.

11. The process as claimed in claim 10, wherein the organic acid is acetic acid.

12. The process as claimed in claim 9, wherein the inorganic acid is a mineral acid.

13. The process as claimed in claim 1, wherein the neutralization reaction in step (c) is carried out in a solvent system containing water and an organic solvent.

14. The process as claimed in claim 13, wherein the organic solvent is selected from the group consisting of ester solvents halogenated hydrocarbon solvents, and hydrocarbon solvents.

15. The process as claimed in claim 14, wherein the organic solvent is methylene chloride, chloroform or ethyl acetate.

16. The process of claim 3 wherein the ester solvent is ethyl acetate, methyl acetate, isopropyl acetate, tert-butyl methyl acetate, ethyl formate, or mixtures thereof.

17. The process of claim 3 wherein the alcoholic solvent is methanol, ethanol, or mixtures thereof.

18. The process of claim 3 wherein the aromatic hydrocarbon solvent is benzene, toluene, xylene, or mixtures thereof.

19. The process of claim 3 wherein the halogenated hydrocarbon solvent is methylene chloride, chloroform, carbontetrachloride, ethylene dichloride, or mixtures thereof.

20. The process of claim 3 wherein the ketonic solvent is acetone, methyl ethyl ketone, methyl isobutyl ketone, diethyl ketone, or mixtures thereof.

21. The process of claim 3 wherein the ether solvent is tert-butyl methyl ether, diethyl ether, diethyl carbonate, or mixtures thereof.

22. The process as claimed in claim 10, wherein the carboxylic acid is acetic acid or formic acid.

23. The process as claimed in claim 10, wherein the sulfonic acid is methane sulfonic acid.

24. The process as claimed in claim 12, wherein the mineral acid is sulfuric acid, hydrochloric acid or phosphoric acid.

25. The process as claimed in claim 14, wherein the ester solvent is ethyl acetate, methyl acetate, isopropyl acetate, tert-butyl methyl acetate, or ethyl formate.

26. The process as claimed in claim 14, wherein the halogenated hydrocarbon solvent is methylene chloride, chloroform, carbontetrachloride, or ethylene dichloride.

27. The process as claimed in claim 14, wherein the hydrocarbon solvent is benzene, toluene, or xylene.

* * * * *